(12) United States Patent
Hirose et al.

(10) Patent No.: US 8,207,348 B2
(45) Date of Patent: Jun. 26, 2012

(54) THIAZOLOTHIAZOLE COMPOUND AND THIAZOLOTHIAZOLE POLYMER

(75) Inventors: Hidekazu Hirose, Kanagawa (JP);
Takeshi Agata, Kanagawa (JP);
Katsuhiro Sato, Kanagawa (JP);
Kazuaki Sato, Yamagata (JP); Yoshihiro Ohba, Yamagata (JP)

(73) Assignee: Fuji Xerox Co., Ltd., Tokyo (JP)

( * ) Notice: Subject to any disclaimer, the term of this patent is extended or adjusted under 35 U.S.C. 154(b) by 4 days.

(21) Appl. No.: 12/780,423

(22) Filed: May 14, 2010

(65) Prior Publication Data
US 2011/0086999 A1    Apr. 14, 2011

(30) Foreign Application Priority Data

Oct. 13, 2009  (JP) .................................. 2009-236603

(51) Int. Cl.
*C07D 513/04*        (2006.01)
(52) U.S. Cl. ........................................................ 548/153
(58) Field of Classification Search ........................ None
See application file for complete search history.

(56) References Cited

U.S. PATENT DOCUMENTS

| 4,092,162 | A | 5/1978 | Wright et al. |
| 4,801,517 | A | 1/1989 | Frechet et al. |
| 4,806,443 | A | 2/1989 | Yanus et al. |
| 4,806,444 | A | 2/1989 | Yanus et al. |
| 4,937,165 | A | 6/1990 | Ong et al. |
| 4,959,228 | A | 9/1990 | Skrgatic et al. |
| 4,983,482 | A | 1/1991 | Ong et al. |
| 5,034,296 | A | 7/1991 | Ong et al. |

FOREIGN PATENT DOCUMENTS

| JP | B2-59-28903 | 7/1984 |
| JP | A-61-20953 | 1/1986 |
| JP | A-1-134456 | 5/1989 |
| JP | A-1-134457 | 5/1989 |
| JP | A-1-134462 | 5/1989 |
| JP | A-4-133065 | 5/1992 |
| JP | A-4-133066 | 5/1992 |
| JP | A-5-80550 | 4/1993 |

OTHER PUBLICATIONS

Gustafsson et al., "Flexible light-emitting diodes made from soluble conducting polymers," *Nature*, Jun. 11, 1992, pp. 477-479, vol. 357.
Sugihara, M. et al., "Synthesis and Physical Properties of Polyphosphazenes Having Hole-Transporting Aromatic Tertiary Amines in Side Chains," Collection of Preliminary Manuscripts 20J21 of 42$^{nd}$ Polymer Discussion Conference, vol. 42, No. 7, 1993, pp. 2860-2863, (with Abstract and partial English-language translation).
"Experimental Chemical Lecture," (edited by the Chemical Society of Japan, and published by Maruzen Co,, Ltd.), 4$^{th}$ ed., vol. 28, pp. 208-231 (with Abstract).

*Primary Examiner* — Kamal Saeed
*Assistant Examiner* — Nyeemah A Grazier
(74) *Attorney, Agent, or Firm* — Oliff & Berridge, PLC

(57) ABSTRACT

The invention provides a thiazolothiazole compound represented by the following Formula (I). In Formula (I), $Ar^1$ represents a substituted or unsubstituted aromatic group; $R^1$ represents a hydrogen atom, an alkyl group, a substituted or unsubstituted aryl group, or a substituted or unsubstituted aralkyl group; and n represents an integer of 0 or 1. The invention further provides a thiazolothiazole polymer having the thiazolothiazole compound as a polymerization unit thereof.

4 Claims, 6 Drawing Sheets

THIAZOLOTHIAZOLE COMPOUND AND THIAZOLOTHIAZOLE POLYMER

CROSS-REFERENCE TO RELATED APPLICATIONS

This application claims priority under 35 USC 119 from Japanese Patent Application No. 2009-236603 filed on Oct. 13, 2009.

BACKGROUND

1. Technical field

The invention relates to a thiazolothiazole compound and a thiazolothiazole polymer having the thiazolothiazole compound as a polymerization unit thereof.

2. Related Art

Various compounds and polymers which have charge transporting property have been known.

SUMMARY

An exemplary embodiment of one aspect of the present invention is (1) a thiazolothiazole compound represented by the following Formula (I).

BRIEF DESCRIPTION OF THE DRAWINGS

Exemplary embodiments of the present invention are described in detail on the following figures, wherein.

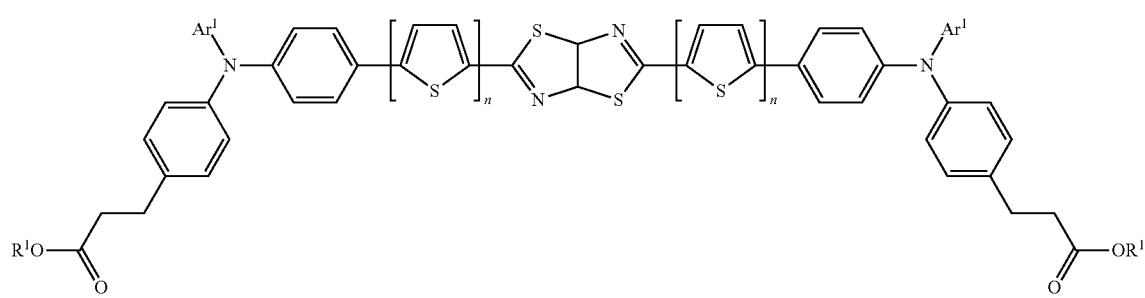

Formula (I)

DETAILED DESCRIPTION

Figure 1:
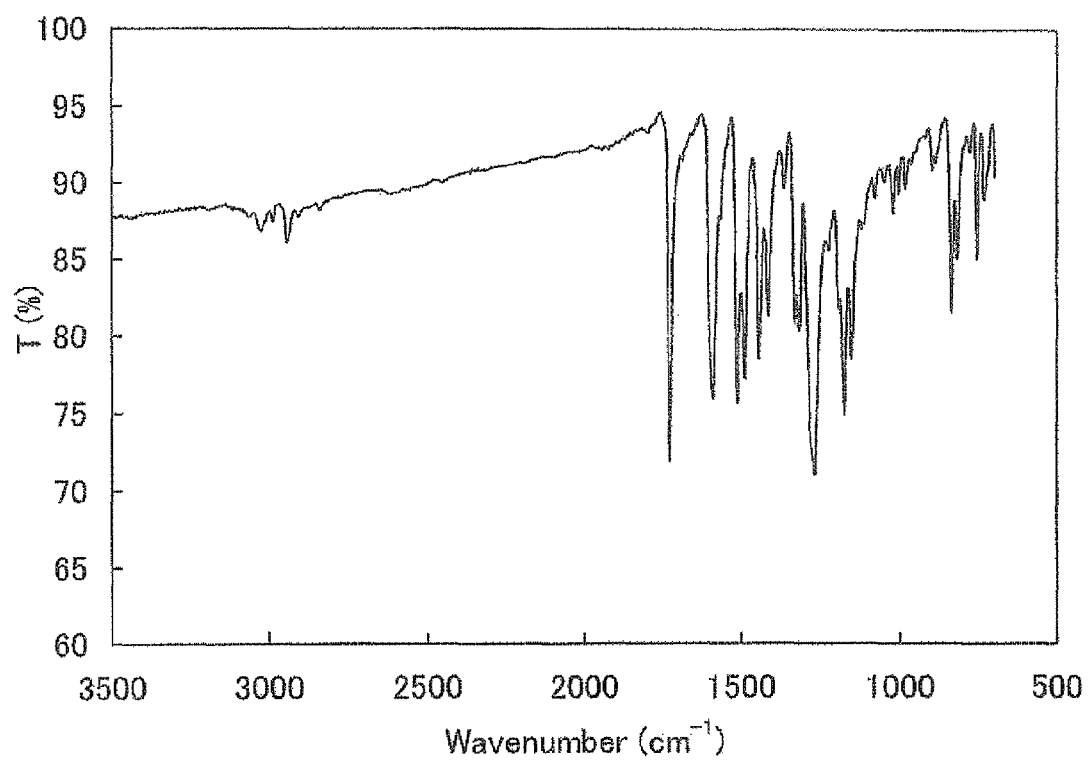
FIG. 1 is an IR absorption spectrum of a compound obtained in Example 1.

An exemplary embodiment of one aspect of the present invention is (1) a thiazolothiazole compound represented by the following Formula (I).

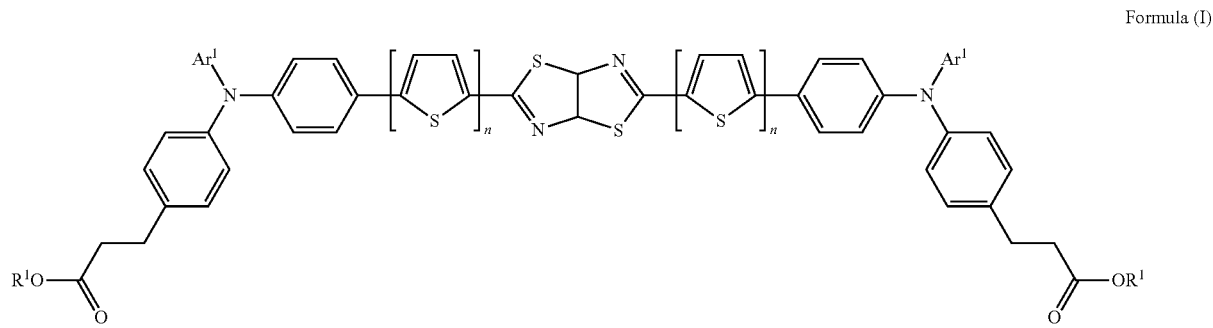

Formula (I)

In Formula (I), $Ar^1$ represents a substituted or unsubstituted aromatic group; $R^1$ represents a hydrogen atom, an alkyl group, a substituted or unsubstituted aryl group, or a substituted or unsubstituted aralkyl group; and n represents an integer of 0 or 1.

In Formula (I), $Ar^1$ represents a substituted or unsubstituted aromatic group; $R^1$ represents a hydrogen atom, an alkyl group, a substituted or unsubstituted aryl group, or a substituted or unsubstituted aralkyl group; and n represents an integer of 0 or 1.

An exemplary embodiment of another aspect of the present invention is (2) a thiazolothiazole polymer represented by the following Formula (II).

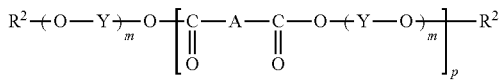

Formula (II)

In Formula (II), Y represents a divalent hydrocarbon group; $R^2$ represents a hydrogen atom, an alkyl group, a substituted or unsubstituted aryl group, or a substituted or unsubstituted aralkyl group; m represents an integer of from approximately 1 to approximately 5; p represents an integer of from approximately 5 to approximately 5000; and A represents a unit represented by the following Formula (III).

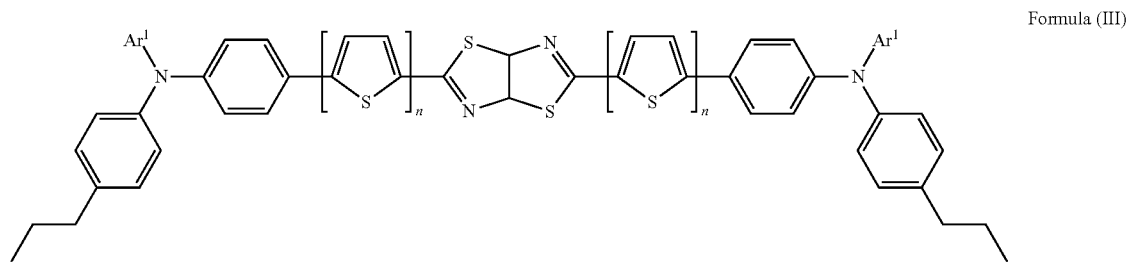

Formula (III)

In Formula (III), $Ar^1$ represents a substituted or unsubstituted monovalent aromatic group; and n represents an integer of 0 or 1.

$Ar^1$ in Formula (I) or Formula (III) represents a substituted or unsubstituted monovalent aromatic group. In embodiments, the aromatic group may contain a heteroring. The number of the aromatic ring(s) and that of the heteroring(s) are not particularly limited. Specific examples of the monovalent aromatic group represented by $Ar^1$ include a substituted or unsubstituted phenyl group, a substituted or unsubstituted monovalent polynuclear aromatic hydrocarbon group having approximately 2 to approximately 20 aromatic rings, a substituted or unsubstituted monovalent condensed aromatic hydrocarbon group having approximately 2 to approximately 20 aromatic rings, a substituted or unsubstituted monovalent aromatic heterocyclic group, and a substituted or unsubstituted monovalent aromatic group having at least one aromatic heteroring.

The "polynuclear aromatic hydrocarbon" herein means a hydrocarbon in which two or more aromatic rings composed of carbon and hydrogen are present and the rings are bonded to each other through a carbon-carbon bond. Specific examples thereof include biphenyl, terphenyl, and stilbene. The "polynuclear aromatic hydrocarbon group" herein means a substituent having a polynuclear aromatic hydrocarbon. Examples thereof include a biphenylene group, which is a substituent having a biphenyl.

The "condensed aromatic hydrocarbon" herein means a hydrocarbon in which two or more aromatic rings composed of carbon and hydrogen are present and the aromatic rings share a pair of adjacent carbon atoms that are bonded to each other. Specific examples thereof include naphthalene, anthracene, phenanthrene, pyrene, perylene, and fluorene. The condensed aromatic hydrocarbon group" herein means a substituent having a condensed aromatic hydrocarbon. Examples thereof include a naphthyl group, which is a substituent having a naphthalene.

The "aromatic heteroring" herein means an aromatic ring which may also contain one or more elements other than carbon and hydrogen.

The kind and the number of the heteroatom(s) (i.e., the atom(s) which (partially) form(s) the cyclic skeleton and is/are other than carbon atoms) are not particularly limited. Examples of the heteroatom include a sulfur atom, a nitrogen atom, and an oxygen atoms. The cyclic skeleton of the aromatic heteroring may contain two or more kinds of heteroatoms, and/or two or more heteroatoms.

Specifically, examples of a heteroring having a 5-membered ring structure include thiophene, thiophine, pyrrole, furan, and a heteroring in which the carbon atoms at the 3- and 4-positions thereof are further substituted with nitrogen atoms. Examples of a heteroring having a 6-membered ring structure include a pyridine ring.

The "aromatic group containing an aromatic heteroring" herein means a linking group which contains, in the atomic group which configures its skeleton, at least one aromatic heteroring defined above. This may be an aromatic group the whole of which is made of a conjugated system, or an aromatic group a part of which is made of a conjugated system. In embodiments, the aromatic group containing an aromatic heteroring may be that the whole of which is made of a conjugated system from the viewpoint of charge transporting performance.

Examples of the substituent which attaches to the aromatic group of the "substituted (or unsubstituted) monovalent aromatic group" include hydrogen, a halogen atom, an alkyl group, an alkoxy group, a phenoxy group, an aryl group, an aralkyl group, an and a substituted amino group. In embodiments, hydrogen, an alkyl group, or an alkoxy group may be specifically used.

Examples of the alkyl group include those having 1 to 10 carbon atoms, and specific examples thereof include a methyl group, an ethyl group, a propyl group, and an isopropyl group.

Examples of the alkoxy group include those having 1 to 10 carbon atoms, and specific examples thereof include a methoxy group, an ethoxy group, a propoxy group, and an isopropoxy group.

Examples of the aryl group include those having 6 to 20 carbon atoms, and specific examples thereof include a phenyl group and a tolyl group.

Examples of the aralkyl group include those having 7 to 20 carbon atoms, and specific examples thereof include a benzyl group and a phenethyl group.

Examples of a substituent of the substituted amino group include an alkyl group, an aryl group, an aralkyl group, and specific examples thereof include those listed for the alkyl group, the aryl group, and the aralkyl group as the substituent of the substituted monovalent aromatic group.

In embodiments, a substituted or unsubstituted phenyl group or a substituted or unsubstituted polynuclear aromatic hydrocarbon group may be used as the monovalent aromatic group represented by each $Ar^1$ in Formulae (I) and (III). In embodiments, a substituted or unsubstituted phenyl group or a substituted or unsubstituted may be used as the monovalent aromatic group represented by each $Ar^1$ in Formulae (I) and (III).

Examples of the divalent carbon group represented by Y in Formula (II) include those represented by any one of the following Formulae (IV-1) to (IV-7).

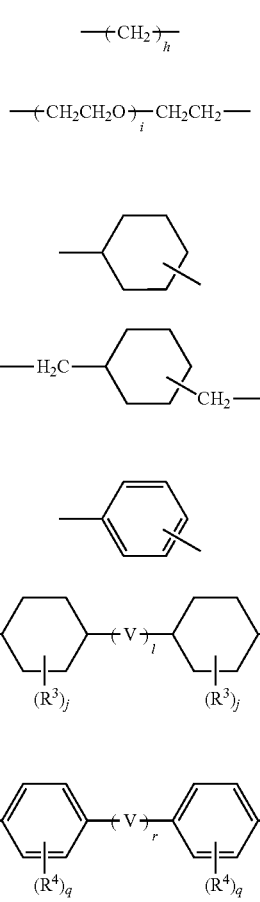

In Formulae (IV-1) to (IV-7), $R^3$(s) and $R^4$(s) each independently represent a hydrogen atom, an alkyl group having approximately 1 to approximately 4 carbon atoms, an alkoxy group having approximately 1 to approximately 4 carbon atoms, a substituted or unsubstituted phenyl group, or a substituted or unsubstituted aralkyl group; h and i each independently represent an integer of approximately 1 to approximately 5; j and q each independently represent an integer of approximately 0 to approximately 6; l and r each independently represent 0 or 1; and v represents a group selected from groups represented by the following Formulae (V-1) to (V-11).

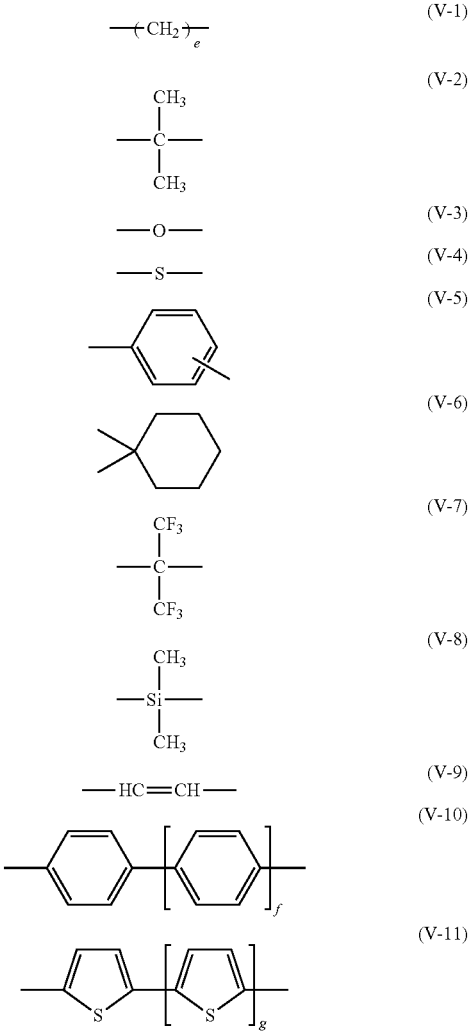

In Formulae (V-1), (V-10) and (V-11), e represents an integer of approximately 1 to approximately 5, and f and g each represent an integer of approximately 0 to approximately 5.

The polymerization degree of the polymer represented by Formula (II) is from approximately 5 to approximately 5,000. In embodiments, the polymerization degree may be from approximately 10 to approximately 1,000 from the viewpoints of the film forming property, the stability of an electric device element formed from the polymer, and the like. In embodiments, the weight-average molecular weight Mw of the polymer represented by Formula (II) may be from approximately 10,000 to approximately 300,000.

$R^1$ in Formula (I) and $R^2$ in Formula (II) each independently represent a hydrogen atom, an alkyl group, a substituted or unsubstituted aryl group, or a substituted or unsubstituted aralkyl group.

Examples of the alkyl group include alkyl groups having 1 to 8 carbon atoms, and specific examples thereof include a methyl group, an ethyl group, an n-propyl group, an isopropyl group, an n-butyl group, a t-butyl group, a pentyl group, a hexyl group, a heptyl group and an octyl group. The alkyl group represented by $R^1$ and $R^2$ may have a linear structure or a branched structure.

Examples of the aryl group include aryl groups having 6 to 20 carbon atoms, and specific examples thereof include a phenyl group and a toluyl group.

Examples of the aralkyl group include aralkyl groups having 7 to 20 carbon atoms, and specific examples thereof include a benzyl group and a phenetyl group.

Examples of the substituent for the substituted aryl group and the substituted aralkyl group include a hydrogen atom, an alkyl group, an alkoxy group, a substituted amino group and a halogen atom.

Specific examples of the thiazolothiazole compound and a thiazolothiazole polymer of the present exemplary embodiment are shown below.

Specific examples of the compound having a structure represented by Formula (I) are shown below, although the present invention is not limited thereby.

TABLE 1

| Structure number | Ar$^1$ | R$^1$ | n |
|---|---|---|---|
| 1 | phenyl | H | 0 |
| 2 | 3,4-dimethylphenyl | H | 0 |
| 3 | 3-methylphenyl | H | 0 |
| 4 | 4-methylphenyl | H | 0 |
| 5 | 3,4,5-trimethylphenyl | H | 0 |
| 6 | 4-biphenyl | H | 0 |
| 7 | 3-methyl-4-methoxy-4′-biphenyl | H | 0 |
| 8 | phenyl | CH$_3$ | 0 |
| 9 | 4-biphenyl | CH$_3$ | 0 |
| 10 | 3-methylphenyl | CH$_3$ | 0 |
| 11 | 4-methylphenyl | CH$_3$ | 0 |
| 12 | 2,3-dimethylphenyl | CH$_3$ | 0 |
| 13 | 4-methoxyphenyl | CH$_3$ | 0 |
| 14 | 9,9-dimethyl-2-fluorenyl | CH$_3$ | 0 |

TABLE 2

| Structure number | Ar$^1$ | R$^1$ | n |
|---|---|---|---|
| 15 | 4-(2-thienyl)phenyl | CH$_3$ | 0 |
| 16 | 3-methyl-4-methoxy-4′-biphenyl | CH$_3$ | 0 |
| 17 | phenyl | n-C$_2$H$_5$ | 0 |
| 18 | 4-methylphenyl | n-C$_2$H$_5$ | 0 |
| 19 | 3-methylphenyl | n-C$_2$H$_5$ | 0 |
| 20 | phenyl | H | 1 |

TABLE 2-continued

| Structure number | Ar¹ | R¹ | n |
|---|---|---|---|
| 21 | H₃CO–C₆H₄– | H | 1 |
| 22 | 9,9-dimethylfluoren-2-yl | H | 1 |
| 23 | biphenyl-4-yl | H | 1 |
| 24 | H₃CO–C₆H₄– | H | 1 |
| 25 | C₆H₅– (phenyl) | CH₃ | 1 |
| 26 | 3-methylphenyl (H₃C–C₆H₄–) | CH₃ | 1 |
| 27 | 4-methylphenyl (H₃C–C₆H₄–) | CH₃ | 1 |
| 28 | biphenyl-4-yl | CH₃ | 1 |

TABLE 3

| Structure number | Ar¹ | R¹ | n |
|---|---|---|---|
| 29 | 9,9-dimethylfluoren-2-yl | CH₃ | 1 |
| 30 | 9,9-dimethyl-7-(4-phenyl)fluoren-2-yl | CH₃ | 1 |
| 31 | 5-(thiophen-2-yl)phenyl | CH₃ | 1 |
| 32 | 4-methoxy-3-methyl-4'-methylbiphenyl derivative (H₃CO, H₃C substituted biphenyl) | CH₃ | 1 |
| 33 | 5-hexyl-thiophen-2-yl-(9,9-dimethylfluoren-2-yl) | CH₃ | 1 |
| 34 | C₆H₅– (phenyl) | n-C₂H₅ | 1 |
| 35 | 3-methylphenyl | n-C₂H₅ | 1 |
| 36 | 4-methylphenyl | n-C₂H₅ | 1 |
| 37 | biphenyl-4-yl | n-C₂H₅ | 1 |

Specific examples of the compound having a structure represented by Formula (II) are shown below, although the present invention is not limited thereby. $R^2$ in Formula (II) for the following specific examples represents a hydrogen atom, an aralkyl group, a substituted or unsubstituted aryl group, or a substituted or unsubstituted aralkyl group. The "structure number" means the structure number of the Exemplary compounds shown in Tables 1 to 3.

TABLE 4

| Polymer | A (Structure number) | Ratio | Y | m | p |
|---|---|---|---|---|---|
| (1) | 1 | — | —CH₂CH₂— | 1 | 23 |
| (2) | 3 | — | 1,2-dimethylcyclohexylene | 1 | 27 |
| (3) | 3 | — | –C₆H₄–CH₂–C₆H₄– | 1 | 22 |
| (4) | 8 | — | —CH₂CH₂— | 1 | 67 |
| (5) | 8 | — | –C₆H₄–CH₂–C₆H₄– | 1 | 21 |
| (6) | 10 | — | —CH₂CH₂— | 1 | 45 |

TABLE 4-continued

| Polymer | A (Structure number) | Ratio | Y | m | p |
|---|---|---|---|---|---|
| (7) | 10 | — | 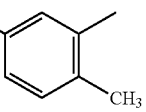 (2-methylphenyl group) | 1 | 24 |
| (8) | 14 | — | —CH$_2$CH$_2$— | 1 | 40 |
| (9) | 14 | — | 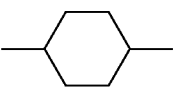 (cyclohexylene) | 1 | 23 |
| (10) | 14 | — | —CH$_2$CH$_2$— | 1 | 55 |
| (11) | 15 | — | 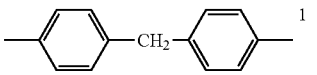 (diphenylmethane) | 1 | 18 |
| (12) | 15 | — | —CH$_2$CH$_2$— | 1 | 60 |
| (13) | 15 | — | —(CH$_2$)$_6$— | 1 | 35 |
| (14) | 16 | — | —CH$_2$CH$_2$— | 1 | 46 |
| (15) | 17 | — | —CH$_2$CH$_2$— | 1 | 48 |
| (16) | 19 | — | 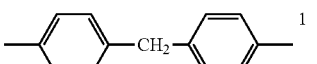 (diphenylmethane) | 1 | 31 |
| (17) | 25 | — | —CH$_2$CH$_2$— | 1 | 36 |
| (18) | 25 | — | —CH$_2$CH$_2$— | 1 | 61 |
| (19) | 25 | — | —(CH$_2$)$_6$— | 1 | 19 |

TABLE 5

| Polymer | A (Structure number) | Ratio | Y | m | p |
|---|---|---|---|---|---|
| (20) | 26 | — | —CH$_2$CH$_2$— | 1 | 51 |
| (21) | 26 | — | 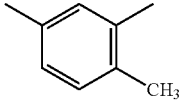 (2-methylphenyl group) | 1 | 22 |
| (22) | 28 | — | —CH$_2$CH$_2$— | 1 | 34 |
| (23) | 31 | — | —(CH$_2$)$_6$— | 1 | 27 |
| (24) | 32 | — | —CH$_2$CH$_2$— | 1 | 38 |
| (25) | 35 | — | —CH$_2$CH$_2$— | 1 | 53 |
| (26) | 36 | — | —CH$_2$CH$_2$— | 1 | 60 |
| (27) | 4/8 | 1/1 | —CH$_2$CH$_2$— | 1 | 35 |
| (28) | 4/14 | 1/1 | —CH$_2$CH$_2$— | 1 | 41 |
| (29) | 8/10 | 1/1 | —CH$_2$CH$_2$— | 1 | 38 |
| (30) | 14/25 | 1/1 | —CH$_2$CH$_2$— | 1 | 36 |

Method of Producing Thiazolothiazole Compound or Thiazolothiazole Polymer

Exemplary methods of producing the thiazolothiazole compound or the thiazolothiazole polymer according to the present exemplary embodiment include: (i) a method including subjecting a formylated triarylamine derivative and rubeanic acid to cyclization reaction; and (ii) a method including: synthesizing a diarylamine by reacting an arylamine with a halogenated carboalkoxyalkylbenzene, or by reacting a halogenated aryl with a carboalkoxyaniline; and reacting the diarylamine with a bis-halogenated aryl.

Examples of the method of introducing a chloromethyl group include: a method including chloromethylazing, after forming a skeleton of a triarylamine, tetraarylbenzidine or the like, a methyl group introduced into a raw material for synthesis at the initial stage of the skeleton; a method including forming a tetraarylbenzidine skeleton using an unsubstituted material, introducing, into the aromatic ring, a functional group such as a formyl group by a substitution reaction, reducing the resultant into an alcohol, and then treating the resultant with a halogenating reagent such as thionyl chloride to induce the alcohol into a chloromethyl group; and a method including subjecting an unsubstituted material to direct chloromethylation by paraformaldehyde and hydrochloric acid.

Exemplary methods of producing the thiazolothiazole compound according to the present exemplary embodiment further include a method including reacting an arylamine or a diarylamine with a halogenated carboalkoxyalkylbenzene. This method may be excellent in enabling easily varying the position of the substituent and regulating the ionization potential and the like. Substituents may be easily introduced into monomers used in this method, and the monomers are chemically stable and thus may be easily handled.

One exemplary embodiment of the method of producing the thiazolothiazole compound according to the present exemplary embodiment will be specifically described hereinafter.

Herein, a triarylamine is obtained by, for example, subjecting a halogenated compound represented by the following Formula (VI) and a diarylamine compound represented by the following Formula (VII) to a coupling reaction in the presence of a copper catalyst, or subjecting a diarylamine compound represented by the following Formula (VIII) and a halogenated compound represented by the following Formula (IX) to a coupling reaction in the presence of a copper catalyst.

Subsequently, the formylated triarylamine derivative represented by Formula (XI) is obtained by reacting the triarylamine derivative represented by Formula (X) with a formylation agent such as N,N-dimethylformamide or N-methylformanilide under the presence of phosphorus oxychloride. By reacting this formylated triarylamine derivative represented by Formula (XI) with rubeanic acid, a thiazolothiazole compound is obtained.

(VI)

(VII)

In Formula (VI), R$^5$ represents a hydrogen atom, an alkyl group, a substituted or unsubstituted aryl group, a substituted or unsubstituted aralkyl group, and G represents a bromine atom or an iodine atom.

In Formula (VII), Ar$^1$ is similar to the Ar$^1$ in Formula (I) or (III), and Ar is similar to the Ar$^{1-}$.

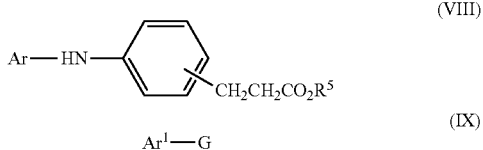

(VIII)

(IX)

In Formula (VIII), $R^5$ represents a hydrogen atom, an alkyl group, a substituted or unsubstituted aryl group, a substituted or unsubstituted aralkyl group, and Ar is similar to the Ar in Formula (VII). In Formula (IX), $Ar^1$ and G are respectively similar to the $Ar^1$ and G in Formulas (VI) and (VII).

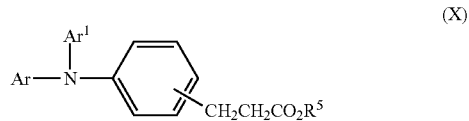

(X)

In Formula (X), $Ar^1$, Ar and $R^5$ are respectively similar to those described above.

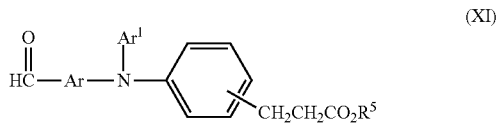

(XI)

In Formula (XI), $Ar^1$, Ar and $R^5$ are respectively similar to those described above.

The amount of the halogen compound represented by Formula (VI) or (IX) used in the coupling reactions may be, for example, from approximately 0.5 equivalents to approximately 1.5 equivalents, and may be preferably from approximately 0.7 equivalents to approximately 1.2 equivalents, for one equivalent of the compound represented by Formula (VII) or (VIII).

Examples of the copper catalyst used in the coupling reactions include copper powder, cuprous oxide, and copper sulfate. The amount of the catalyst may be, for example, from approximately 0.001 parts by weight to approximately 3 parts by weight, and may be preferably in an amount of from approximately 0.01 parts by weight to approximately 2 parts by weight, with respect to 1 part by weight of the compound represented by Formula (VII) or (VIII).

Specific examples of the base used in the coupling reactions include sodium hydroxide, potassium hydroxide, sodium carbonate, and potassium carbonate. The amount of the base may be, for example, from approximately 0.5 equivalents to approximately 3 equivalents, and may be preferably from approximately 0.7 equivalents to approximately 2 equivalents, with respect to 1 equivalent of the compound represented by Formula (VII) or (VIII).

In the coupling reactions, a solvent may be used or may not be used.

Examples of the solvent include water-insoluble hydrocarbon solvents having high boiling point such as n-tridecane, tetralin, p-cymene and terpinolene, and halogen-containing solvents having high boiling point such as o-dichlorobenzene and chlorobenzene. The amount of the solvent may be, for example, from approximately 0.1 parts by weight to approximately 3 parts by weight, and may be preferably from approximately 0.2 parts by weight to approximately 2 parts by weight, with respect to 1 part by weight of the compound represented by Formula (VII) or (VIII).

The coupling reactions may be conducted at a temperature of, for example, from 100° C. to 300° C., may be preferably from 150° C. to 270° C., and may be more preferably from 180° C. to 230° C., under the atmosphere of an inert gas such as nitrogen or argon with the reaction solution being sufficiently effectively stirred. In embodiments, the reaction may be performed with removing water generated during the reaction.

After the completion of the coupling reactions, which may be followed by cooling if necessary, the resultant may be subjected to hydrolysis reaction using a solvent such as methanol, ethanol, n-octanol, ethylene glycol, propylene glycol or glycerin, and a base such as sodium hydroxide or potassium hydroxide.

The amount of the solvent used in the hydrolysis reaction may be, for example, from 0.5 parts by weight to 10 parts by weight, and may be preferably from 1 part by weight to 5 parts by weight, with respect to 1 part by weight of the compound represented by Formula (VII) or (VIII). The amount of the base used in the hydrolysis reaction may be, for example, from 0.2 parts by weight to 5 parts by weight, and may be preferably from 0.3 parts by weight to 3 parts by weight, with respect to 1 part by weight of the compound represented by Formula (VII) or (VIII).

The hydrolysis reaction is performed, after the coupling reaction is conducted, by directly adding the solvent and the base to the reaction solution and stirring the mixture at a temperature of 50° C. or higher and lower than the boiling temperature of the solvent under the atmosphere of an inert gas such as nitrogen or argon.

A carboxylic acid salt which is generated during the coupling reaction may solidify during the coupling reactions. In consideration of this, a solvent having a boiling temperature of 150° C. or higher may be used as the solvent in the hydrolysis reaction in view of raising the reaction temperature.

After completion of the hydrolysis reaction, the reaction solution is poured into water and neutralized using hydrochloric acid or the like so that a triarylamine compound represented by Formula (X) is released.

In embodiments, a water-soluble solvent such as ethylene glycol, propylene glycol or glycerin may be further added in the post treatment including the pouring and neutralizing after completion of the hydrolysis reaction to release the triarylamine compound represented by Formula (X).

Thereafter, the resultant is washed, and may be further subjected to either a column purification using an adsorbent such as silica gel, alumina, activated clay, activated carbon or the like, or a treatment in which such an adsorbent is added to the reaction resultant solution so as to adsorb unnecessary components if necessary. The resultant may be further subjected to a recrystallization using an appropriate solvent such as acetone, ethanol, ethyl acetate, or toluene, or a process including esterifying the resultant to a methyl-ester, an ethyl-ester or the like and then recrystallizing the esterified resultant in a similar manner as the recrystallization.

Subsequently, the formylated triarylamine derivative represented by Formula (XI) is obtained by reacting the triarylamine compound represented by Formula (X), which is obtained in the above process, with a formylation agent such as N,N-dimethylformamide or N-methylformanilide under the presence of phosphorus oxychloride. In this case, the formylation agent may be used also as a reaction solvent by using an excessive amount thereof. Alternatively, a solvent that is inactive with respect to reaction, such as o-dichlorobenzene, benzene or methylene chloride, may be used as the solvent. The reaction temperature may be, for example, from 0° C. to the boiling temperature of the solvent used in the reaction, and may be preferably from 27° C. to 150° C.

Next, the thiazolothiazole compound represented by Formula (I) is obtained by subjecting the formylated triarylamine derivative represented by Formula (XI) and rubeanic acid to cyclization reaction.

In the cyclization reaction of the formylated triarylamine derivative represented by Formula (XI) and rubeanic acid, the rubeanic acid is used in an amount of, for example, from 1.5 equivalents to 5.0 equivalents, preferably from 1.7 equivalents to 4 equivalents, with respect to 1 equivalent of the compound represented by Formula (XI).

A solvent may be used or may not be used in the coupling reaction. Examples of the solvent include water-insoluble hydrocarbon solvents having high boiling temperature such as n-tridecane, tetralin, p-cymene and terpinolene, and halogen-containing solvents having high boiling temperature such as o-dichlorobenzene and chlorobenzene. The solvent may be in an amount of from 0.1 parts by weight to 3 parts by weight, and may be more preferably in an amount of from 0.2 parts by weight to 2 parts by weight for 1 part by weight, with respect to 1 parts by weight of the formylated triarylamine derivative represented by Formula (XI).

The coupling reaction may be performed at, for example, from 100° C. to 300° C., preferably from 150° C. to 270° C., and may more preferably from 180° C. to 250° C., under the atmosphere of an inert gas such as nitrogen or argon, with sufficiently effectively stirring the reaction solution. In embodiments, the coupling reaction may be performed with removing water generated in the reaction.

Methods of the thiazolothiazole polymer according to the present exemplary embodiment may be as follows.

sulfonic acid, or trifluoroacetic acid. The catalyst may be used in an amount of from 1/10,000 parts by weight to 1/10 parts by weight, and may be preferably from 1/1,000 parts by weight to 1/50 parts by weight, with respect to 1 part by weight of the low molecular weight compound represented by Formula (XIV).

In embodiments, a solvent azeotropic with water may be used in order to remove water generated in the synthesis. Examples of the solvent include toluene, chlorobenzene, and 1-chloronaphthalene. The solvent may be used in an amount of from 1 part by weight to 100 parts by weight, and may be preferably from 2 parts by weight to 50 parts by weight, with respect to 1 part by weight of the low molecular weight compound represented by Formula (XIV).

The reaction temperature is not particularly limited. In embodiments, the reaction may be performed at the boiling temperature of the solvent in order to remove water generated in the polymerization.

When no solvent is used in the reaction, the reaction product is dissolved into a solvent after the completion of the reaction, and the resultant solution is used in following processes. When the solvent is used in the reaction, the reaction solution is used as it is in following processes. The resultant solution or the reaction solution is added dropwise to an alcohol such as methanol or ethanol or a poor solvent in which the polymer is slightly dissolved such as acetone so that a polymer is precipitated. The polymer is separated, and subsequently the polymer is sufficiently washed with water or an organic solvent and then dried. If necessary, it is allowable to repeat a reprecipitation treatment including dissolving the polymer into an appropriate organic solvent and adding the solution dropwise to a poor solvent so as to precipitate the polymer. In the reprecipitation treatment, the solution may be effectively stirred with a mechanical stirrer or the like. An

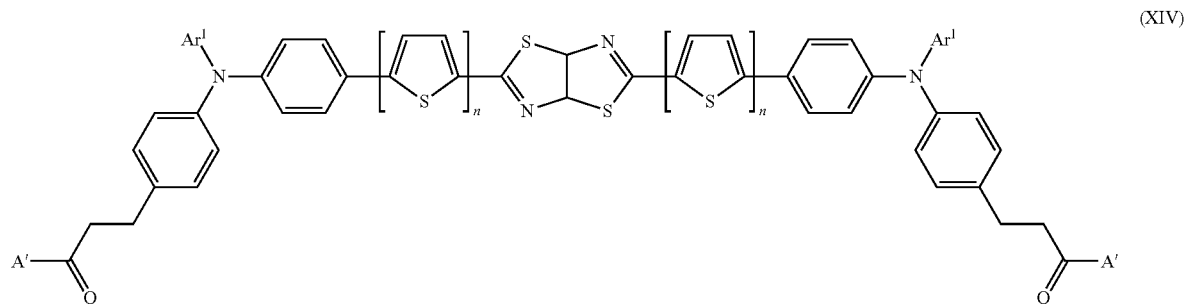

In Formula (XIV), each $Ar^1$ is similar to $Ar^1$ in Formula (I), each A' independently represents a hydroxyl group, a halogen atom, or a group —O—$R^6$, in which $R^6$ represents an alkyl group, a substituted or unsubstituted aryl or a substituted or unsubstituted aralkyl group.

Specifically, the thiazolothiazole polymer represented by Formula (II) may be synthesized as follows.

<1> In the case that A' represents a hydroxyl group:

In the case that A' is a hydroxyl group, the thiazolothiazole polymer represented by Formula (II) may be formed by mixing a compound represented by Formula (XIV) with a bivalent alcohol represented by HO—(Y—O)m-H, an amount of which being an equivalent amount to that of the compound represented by Formula (XIV), and polymerizing these using an acidic catalyst. Herein, m and Y in the bivalent alcohol HO—(Y—O)m-H are respectively the same as those in Formula (II).

Examples of the acidic catalyst include those used in ordinary esterification reaction, such as sulfuric acid, toluene-amount of the solvent in which the polymer is dissolved in the reprecipitation treatment may be from 1 part by weight to 100 parts by weight, and may be preferably from 2 parts by weight to 50 parts by weight, with respect to 1 part by weight of the polymer. An amount of the poor solvent may be from 1 part by weight to 1,000 parts by weight, and may be preferably from 10 parts by weight to 500 parts by weight, with respect to 1 part by weight of the polymer.

<2> In the case that A' represents a halogen:

In the case that A' is a halogen, the thiazolothiazole polymer represented by Formula (II) may be formed by mixing a compound represented by Formula (XIV) with a bivalent alcohol represented by HO—(Y—O)m-H, an amount of which being an equivalent amount to that of the compound represented by Formula (XIV), and polymerizing these using an organic basic catalyst such as pyridine or triethylamine. Herein, m and Y in the bivalent alcohol HO—(Y—O)m-H are respectively the same as those in Formula (II).

The organic basic catalyst may be used in an amount of from 1 part by weight to 10 parts by weight, and may be preferably from 2 parts by weight to 5 parts by weight, with respect to 1 part by weight of the low molecular weight compound represented by Formula (XIV).

Examples of a solvent which may be used in the polymerization include methylene chloride, tetrahydrofuran (THF), toluene, chlorbenzene, and 1-chloronaphthalene. The solvent may be used in an amount of from 1 part by weight to 100 parts by weight, and may be preferably from 2 parts by weight to 50 parts by weight, with respect to 1 part by weight of the low molecular weight compound represented by Formula (XIV).

The reaction temperature is not particularly limited. After the polymerization, the resultant is subjected to a reprecipitation treatment in the same manner as described above so as purify the polymer.

When a bivalent alcohol having a high acidity, such as bisphenopl, is used as the bivalent alcohol represented by HO—(Y—O)m-H, the polymerization may be performed by interfacial polymerization.

The interfacial polymerization may be performed by adding water to the bivalent alcohol, adding a base thereto in an amount equivalent to that of the bivalent alcohol, dissolving the base to the solution, and adding, to the solution, a solution of the low molecular weight compound represented by Formula (XIV), the amount of which being equivalent to that of the bivalent alcohol, with vigorously stirring the solution, whereby polymerization is carried out. An amount of water used herein may be, for example, from 1 part by weight to 1,000 parts by weight, and may be preferably from 2 parts by weight to 500 parts by weight, with respect to 1 part by weight of the bivalent alcohol. Examples of the solvent in which the low molecular weight compound is dissolved include methylene chloride, dichloroethane, trichloroethane, toluene, chlorobenzene, and 1-chloronaphthalene. The reaction temperature is not particularly limited. A phase transfer catalyst such as an ammonium salt or a sulfonium salt may be used in order to promote the reaction. An amount of the phase transfer catalyst used herein may be, for example, from 0.1 parts by weight to 10 parts by weight, and may be preferably from 0.2 parts by weight to 5 parts by weight for 1 part by weight, with respect to 1 part by weight of the monomer.

<3> In the case that A' represents —O—$R^6$:

In the case that A' is —O—$R^6$, the thiazolothiazole polymer represented by Formula (II) may be formed by mixing a compound represented by Formula (XIV) with an excessive amount of a bivalent alcohol represented by HO—(Y—O)m-H, and heating these with using, as a catalyst, an inorganic acid such as sulfuric acid or phosphoric acid, an alkoxide titanium, an acetate salt or carbonate salt of calcium, cobalt or the like, or a zinc oxide, thereby causing a transesterification reaction. Herein, m and Y in the bivalent alcohol HO—(Y—O)m-H are respectively the same as those in Formula (II).

The bivalent alcohol may be used in an amount of from 2 equivalents to 100 equivalents, and may be preferably from 3 equivalents to 50 equivalents, with respect to 1 equivalent of the low molecular weight compound represented by Formula (XIV). The catalyst may be used in an amount of from 1/1,000 parts by weight to 1 part by weight, and may be preferably from 1/100 parts by weight to 1/2 parts by weight, with respect to 1 part by weight of the low molecular weight compound represented by Formula (XIV). The transesterification reaction may be performed at a reaction temperature of, for example, from 200° C. to 300° C. After the completion of the transesterification of the group —O—$R^6$ to a group —O—(Y—O)m-H, the reaction system may be subjected to a reduced pressure in order to promote a polymerization reaction by leaving of HO—(Y—O)m-H. In embodiments, a high boiling temperature solvent azeotropic with HO—(Y—O)m-H, such as 1-chloronaphthalene, may be used to conduct the reaction with removing HO—(Y—O)m-H by azeotropy under a reduced pressure.

Alternatively, the thiazolothiazole polymer represented by Formula (II) may be synthesized as follows. In any one of the cases <1> to <3>, an excessive amount of the bivalent alcohol is added to the low molecular weight compound represented by Formula (XIV) to cause the two components to react with each other, thereby producing a compound represented by the following Formula (XV). Then, the compound represented by Formula (XV) is reacted with a bivalent carboxylic acid, a bivalent carboxylic halide or the like in the similar manner as in the case <2>, with using the compound represented by Formula (XV) in place of the low molecular weight compound represented by Formula (XIV), to obtain the thiazolothiazole polymer.

(XV)

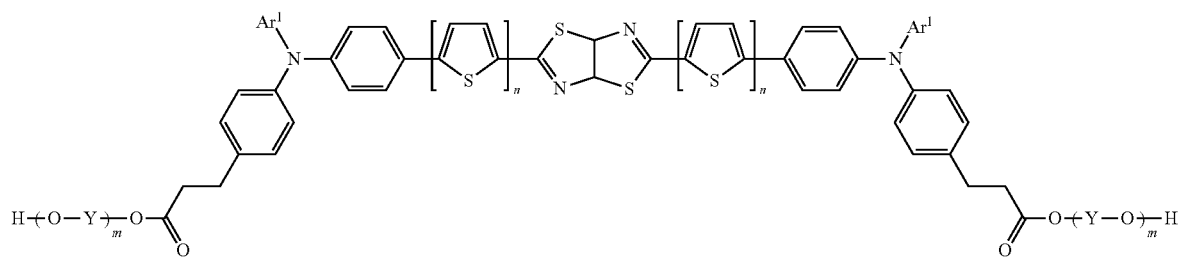

In Formula (XV), each $Ar^1$ and each n are similar to each $Ar^1$ and each n in Formula (I) respectively, and each Y and each m are similar to each Y and each m in Formula (II) respectively.

EXAMPLES

Hereinafter, the present invention will be described by way of the following examples; however, the invention is not limited thereto.

Example 1

Acetoanilide (25.0 g), methyl 4-iodophenylpropionate (64.4 g), potassium carbonate (38.3 g), copper sulfate pentahydride (2.3 g), and n-tridecane (50 mL) are put into a 500 mL three-necked flask, and then the solution is heated and stirred under nitrogen gas flow at 230° C. for 20 hours. After the completion of the reaction, potassium hydroxide (15.6 g) dissolved in ethylene glycol (300 mL) is added to the solution, and then the solution is heated to reflux under nitrogen gas flow for 3.5 hours. Thereafter, the system is cooled to room temperature (25° C.), and the reaction solution is poured into 1 L of distilled water. The resultant is neutralized with hydrochloric acid to precipitate a crystal. The crystal is collected by suction filtration, sufficiently washed with water, and transferred to a 1 L flask. Toluene (500 mL) is added thereto, and the solution is heated to reflux. Then, water is removed by azeotropic removal, and then a solution in which concentrated sulfuric acid (1.5 mL) is dissolved in methanol (300 mL) is added thereto. The resultant solution is heated to reflux under nitrogen gas flow for 5 hours. After the reaction, the resultant is subjected to extraction with toluene. The resultant organic phase is sufficiently washed with pure water. Next, the layer is dried with anhydrous sodium sulfate. The solvent is distilled off therefrom under a reduced pressure. The resultant is recrystallized using hexane to yield 36.5 g of DAA-1 shown below.

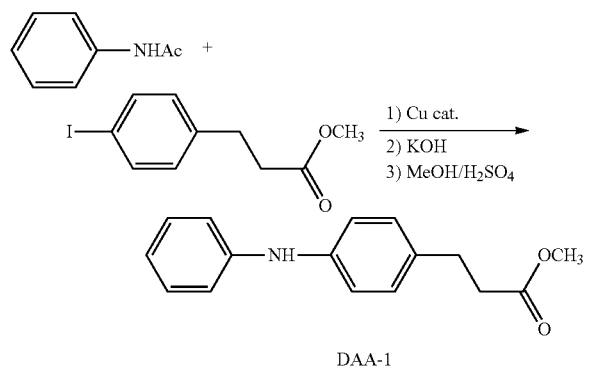

Subsequently, a mixed solution of iodobenzene (4.8 g), the DAA-1 (5.0 g), copper (II) sulfate pentahydrate (0.2 g), potassium carbonate (1.3 g) and tridecane (10 ml) is stirred at 210° C. for 7 hours. After the completion of reaction, a solution prepared by dissolving potassium hydroxide (15.6 g) in ethylene glycol (300 ml) is added to the reaction solution. After heating to reflux for 3.5 hours under a nitrogen stream, the reaction solution is cooled to room temperature (25° C.) and poured in 1 L of distilled water. This resultant is neutralized with hydrochloric acid and a crystal is allowed to precipitate. The crystal is collected by suction filtering and washed with water, and then placed in a 1 L flask. Toluene (500 ml) is added thereto and heated to reflux. After removing water by azeotropic removal, a solution of concentrated sulfuric acid (1.5 ml) and methanol (300 ml) is added thereto, and the mixture is heated to reflux for 5 hours under a nitrogen stream. The mixture is cooled (25° C.) and toluene is added thereto, and filtered with sellite. The resultant is washed with pure water and an organic phase is extracted. A product obtained by distilling away the organic solvent is separated by silica gel column chromatography (hexane: toluene=4:1), thereby obtaining 3.9 g of TAA-1 shown below.

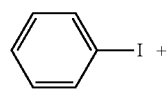

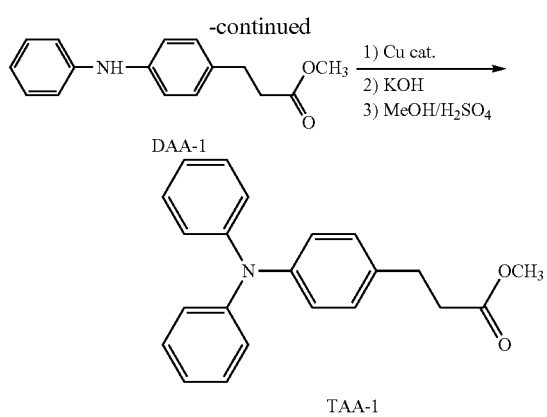

A mixed solution of TAA-1 (3.0 g) and N,N-dimethylformamide (100 ml) is placed in a 500-ml three-neck flask. After dropping phosphorous oxychloride (1.7 g) therein, the mixed solution is heated to 80° C. and stirred for 7 hours.

After cooling, the reaction solution is added to pure water and a crystal is allowed to precipitate. The crystal is collected by suction filtering, thereby obtaining 2.4 g of formylated TAA-1.

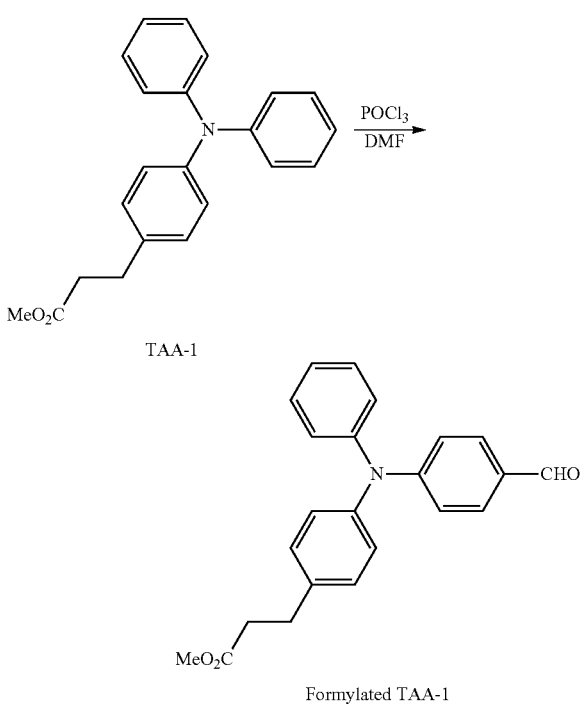

Under a nitrogen stream, formylated TAA-1 (2.0 g) and rubeanic acid (0.37 g) are dissolved in mesitylene (5 ml), and the mixture is refluxed for 30 hours. A solid obtained by distilling away the mesitylene under reduced pressure is subjected to Soxhlet extraction with hexane (6 hours) in order to remove impurities. Subsequently, the resultant is subjected to Soxhlet extraction with toluene (4.5 hours). The thus-obtained crude crystal is separated by silica gel column chromatography (toluene:ethyl acetate=20:1) and recrystallized using toluene, thereby obtaining 0.62 g of Exemplary compound 8.

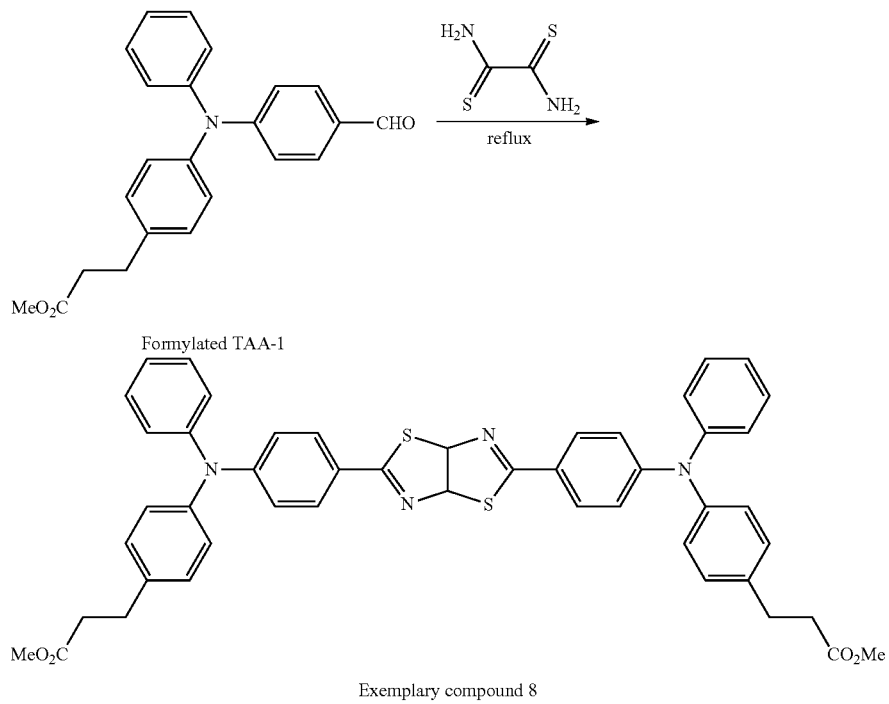

Exemplary compound 8

Figure 2:
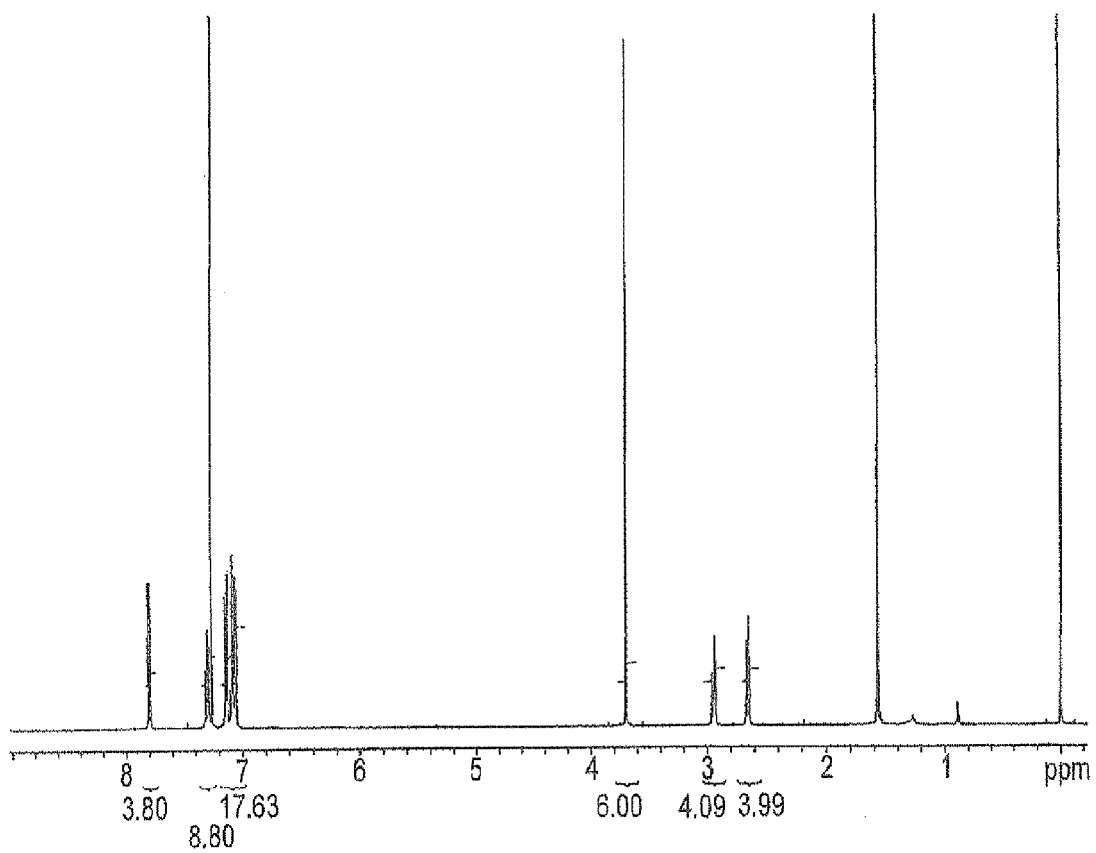
FIG. 2 is a $^1$H-NMR spectrum of the compound obtained in Example 1.

The melting temperature of Exemplary compound 8 is in a range of from 191° C. to 192° C. The infrared absorption spectrum of Exemplary compound 8 is shown in FIG. 1, and the $^1$H NMR spectrum thereof ($^1$H-NMR, solvent: CDCl$_3$, the same being applied correspondingly to any NMR spectrum in the following) is shown in FIG. 2.

The ionization potential of the compound of Exemplary compound 8 is 5.60 eV, the hole mobility thereof is $5.24 \times 10^{-6}$ cm$^2$/Vs, and the electron mobility thereof is $7.37 \times 10^{-6}$ cm$^2$/Vs.

Peaks in the IR spectrum obtained using Attenuated Total Reflectance (ATR) method reside at 756 cm$^{-1}$, 836 cm$^{-1}$, 1176 cm$^{-1}$, 1269 cm$^{-1}$, 1510 cm$^{-1}$, 1590 cm$^{-1}$, 1725 cm$^{-1}$, 2945 cm$^{-1}$, and 3034 cm$^{-1}$.

Peaks in the $^1$H-NMR spectrum using CDCl$_3$ solvent reside at 2.62-2.70 (4H), 2.75-2.96 (4H), 3.65-3.69 (6H), 7.00-7.15 (17H), 7.20-7.32 (5H), and 7.76-7.82 (4H).

The ionization potential is measured by photoemission yield spectroscopy in air using a measurement device (trade name: AC-2, manufactured by Riken Keiki Co., Ltd.).

The $^1$H-NMR spectra are measured by a measurement device (trade name: UNITY-300 (300 MHz), manufactured by Varian, Inc.).

The IR spectra are measured by ATR method using a Fourier transform infrared spectrophotometer (trade name: TF/IR-6100, manufactured by JASCO Corporation, ATR prism: ZnSe45°, resolution: 4 cm$^{-1}$).

The hole mobility and the electron mobility are measured with a device for the time-of-flight method (trade name: TOF-401, manufactured by Optel Co., Ltd., excitation light source: nitrogen pulsed laser (wavelength: 337 nm), applied voltage: 30V/μm). The hole mobility measurement about each of the compounds is performed by using a film in which 40% by mass of the compound is dispersed in polycarbonate unless otherwise specified.

The electron mobility measurement about each of the compounds is performed under vacuum ($10^{-3}$ Torr).

These measurement methods are employed throughout the Examples.

Example 2

4-(2-Thienyl)acetoanilide (30.0 g), methyl 4-iodophenyl-propionate (28.5 g), potassium carbonate (13.6 g), copper sulfate pentahydride (2.0 g), and 1,2-dichlorobenzene (50 mL) are put into a 500 mL three-necked flask, and then the solution is heated and stirred under nitrogen gas flow at 230° C. for 20 hours. After the completion of the reaction, potassium hydroxide (15.6 g) dissolved in ethylene glycol (300 mL) is added to the solution, and then the solution is heated to reflux under nitrogen gas flow for 3.5 hours. Thereafter, the system is cooled to room temperature (25° C.), and the reaction solution is poured into 1 L of distilled water. The resultant is neutralized with hydrochloric acid to precipitate a crystal. The crystal is collected by suction filtration, sufficiently washed with water, and transferred to a 1 L flask. Toluene (500 mL) is added thereto, and the solution is heated to reflux. Then, water is removed by azeotropic removal, and then a solution in which concentrated sulfuric acid (1.5 mL) is dissolved in methanol (300 mL) is added thereto. The resultant solution is heated to reflux under nitrogen gas flow for 5 hours. After the reaction, the resultant is subjected to extraction with toluene. The resultant organic phase is sufficiently washed with pure water. Next, the layer is dried with anhydrous sodium sulfate. The solvent is distilled off therefrom under a reduced pressure. The resultant is recrystallized using hexane to yield 17.9 g of DAA-2 shown below.

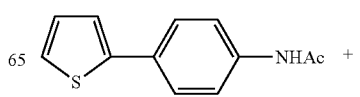

-continued

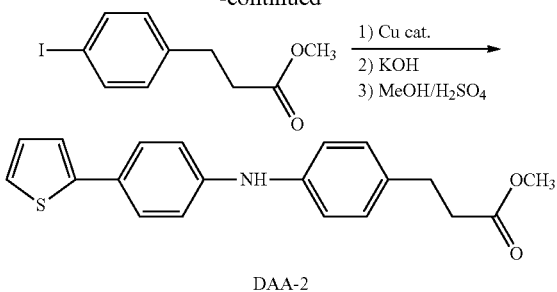

DAA-2

Subsequently, a mixed solution of iodobenzene (3.6 g), the DAA-2 (5.0 g), copper (II) sulfate pentahydrate (0.2 g), potassium carbonate (1.3 g) and tridecane (15 ml) is stirred at 210° C. for 15 hours.

After the completion of reaction, a solution prepared by dissolving potassium hydroxide (15.6 g) in ethylene glycol (300 ml) is added to the reaction solution. After heating to reflux for 3.5 hours under a nitrogen stream, the reaction solution is cooled to room temperature (25° C.) and poured in 1 L of distilled water. This resultant is neutralized with hydrochloric acid and a crystal is allowed to precipitate. The crystal is collected by suction filtering and washed with water, and then placed in a 1 L flask. Toluene (500 ml) is added thereto and heated to reflux. After removing water by azeotropic removal, a solution of concentrated sulfuric acid (1.5 ml) and methanol (300 ml) is added thereto, and the mixture is heated to reflux for 5 hours under a nitrogen stream.

The mixture is cooled (25° C.) and toluene is added thereto, and filtered with sellite. A product obtained by distilling away toluene the from the resultant is separated by silica gel column chromatography (hexane:toluene=2:1), thereby obtaining 3.2 g of TAA-2 shown below.

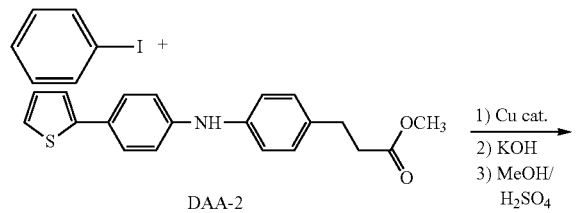

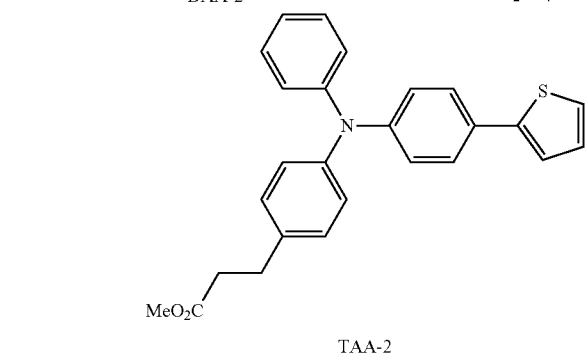

TAA-2

TAA-2 (3.0 g) is dissolved in N,N-dimethylformamide (5 ml) and phosphorous oxychloride is dropped therein. After stirring the mixture at 25° C. for 4 hours, anhydrous N,N-dimethylformamide (3 ml) is added thereto and the mixture is further stirred using a magnetic stirrer for 13.5 hours. After the completion of reaction, water (100 ml) and ethyl acetate (100 ml) are added and stirred, and an organic phase is separated. The organic phase is washed with 50 ml of saturated saline and dried with sodium sulfate. The crude product obtained by distilling away the solvent is separated by silica gel column chromatography (ethyl acetate:hexane=1:4), thereby obtaining 2.5 g of formylated TAA-2.

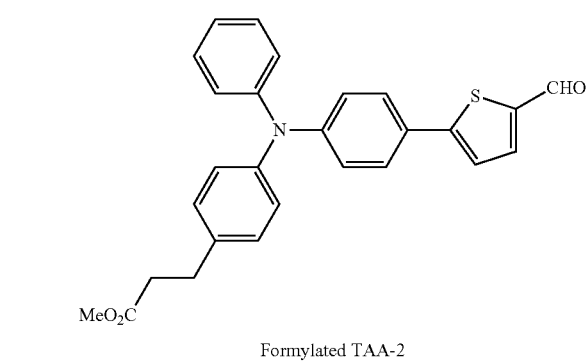

The formylated TAA-2 (2.2 g) and rubeanic acid (0.37 g) are dissolved in mesitylene (5 ml), and the mixture is refluxed for 30 hours. A solid obtained by distilling away the mesitylene under reduced pressure is subjected to Soxhlet extraction with hexane (6 hours) in order to remove impurities. The thus-obtained crude crystal is separated by silica gel column chromatography (toluene:ethyl acetate=20:1) and recrystallized using toluene, thereby obtaining 0.54 g of Exemplary compound 25.

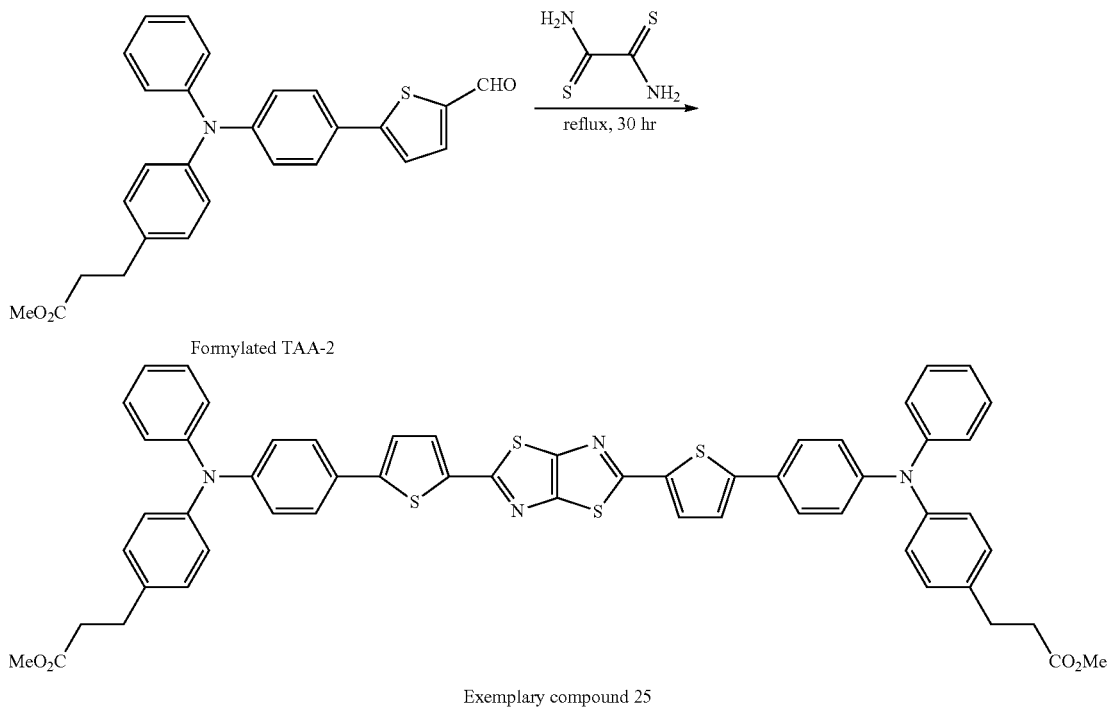

Exemplary compound 25

Figure 3:
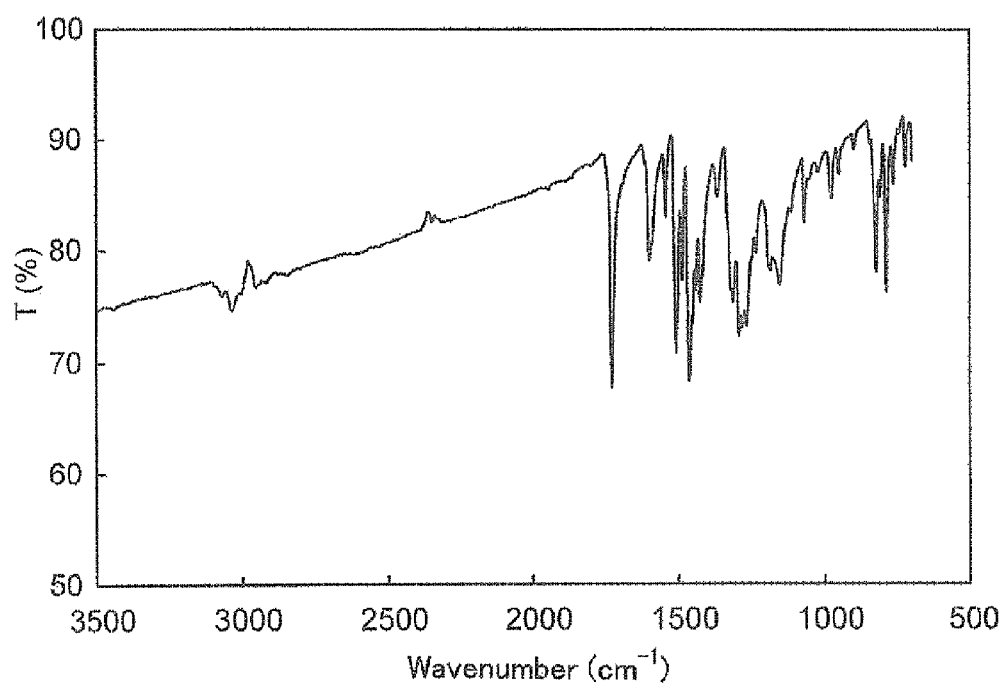
FIG. 3 is an IR absorption spectrum of a compound obtained in Example 2.
Figure 4:
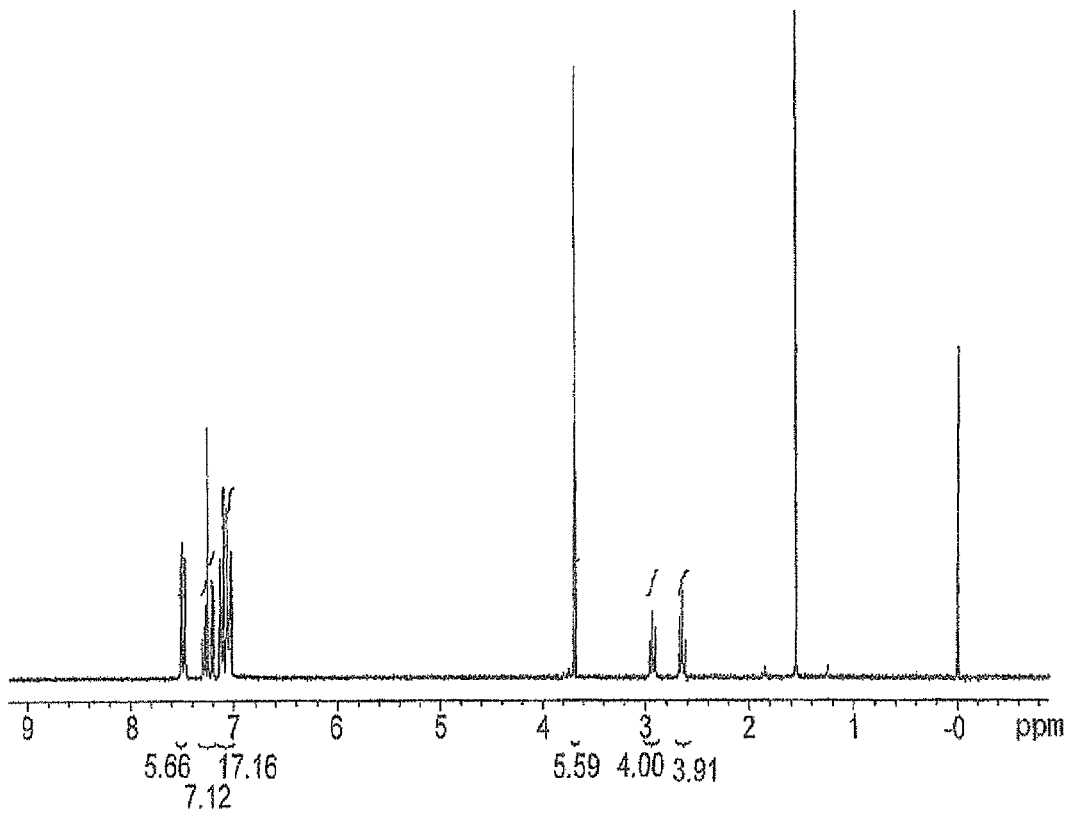
FIG. 4 is a $^1$H-NMR spectrum of the compound obtained in Example 2.

The melting temperature of Exemplary compound 25 is in a range of from 227° C. to 228° C. The infrared absorption spectrum of Exemplary compound 25 is shown in FIG. 3, and the $^1$H NMR spectrum thereof ($^1$H-NMR, solvent: CDCl$_3$, the same being applied correspondingly to any NMR spectrum in the following) is shown in FIG. 4.

The ionization potential of the compound of Exemplary compound 25 is 5.39 eV, the hole mobility thereof is $6.18 \times 10^{-6}$ cm$^2$/Vs, and the electron mobility thereof is $7.10 \times 10^{-6}$ cm$^2$/Vs.

Peaks in the IR spectrum obtained using ATR method reside at 787 cm$^{-1}$, 1157 cm$^{-1}$, 1294 cm$^{-1}$, 1463 cm$^{-1}$, 1727 cm$^{-1}$, 2957 cm$^{-1}$, and 3040 cm$^{-1}$.

Peaks in the $^1$H-NMR spectrum using CDCl$_3$ solvent reside at 2.60-2.71 (4H), 2.72-2.96 (4H), 3.65-3.70 (6H), 7.00-7.15 (17H), 7.20-7.28 (7H), and 7.40-7.52 (6H).

Example 3

Into a 50 mL three-necked eggplant shaped flask are put 1.0 g of Exemplary compound 8, 10 mL of ethylene glycol, and 0.02 g of tetrabutoxytitanium, and then the solution is heated and stirred at 200° C. for 5 hours under the atmosphere of nitrogen.

After ascertaining by TLC that the raw material Exemplary compound 8 disappears, the pressure is reduced to 50 Pa to distill off ethylene glycol with heating the solution to 210° C. to continue the reaction for 6 hours.

Thereafter, the system is cooled to room temperature (25° C.), and the resultant is dissolved in 50 mL of tetrahydrofuran. Insoluble matters are filtrated off using a polytetrafluoroethylene (PTFE) filter having a pore size of 0.5 μm. The filtrate is distilled under a reduced pressure, and then the residue is dissolved into 300 mL of monochlorobenzene. The resultant is washed once with 300 mL of 1 N HCl and further three times with 500 mL of water successively. The monochlorobenzene solution is distilled to 30 mL under a reduced pressure, and the residue is added dropwise to 800 mL of a mixture solvent (ethyl acetate:methanol=1:3) to reprecipitate a polymer.

The resultant polymer is collected by filtration, and then washed with methanol. Thereafter, the resultant is subjected to vacuum drying at 60° C. for 16 hours to yield 0.7 g of thea polymer (Exemplary compound 4).

The molecular weight of this polymer is measured with a device for gel permeation chromatography (GPC) (trade name: HLC-8120 GPC, manufactured by Tosoh Corp.). As a result, the weight-average molecular weight Mw is $5.7 \times 10^4$ (in terms of styrene). The molecule distribution Mw/Mn is 1.21, and the polymerization degree p calculated from the molecular weight of the low molecular weight monomer is 71.

Figure 5:
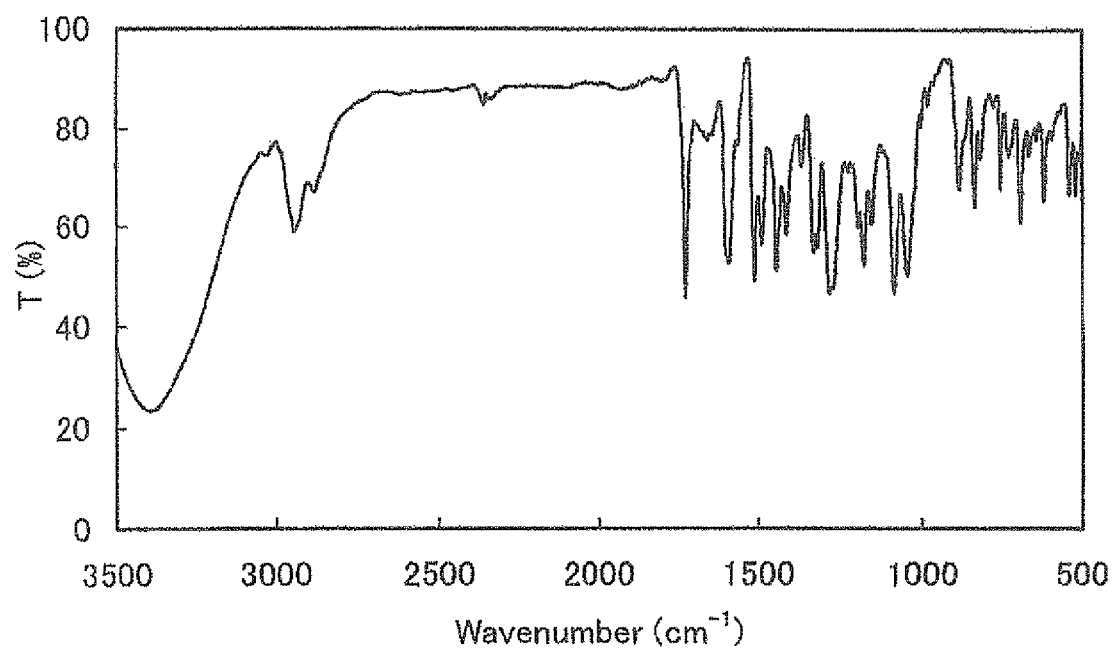
FIG. 5 is an IR absorption spectrum of a compound obtained in Example 3.
Figure 6:
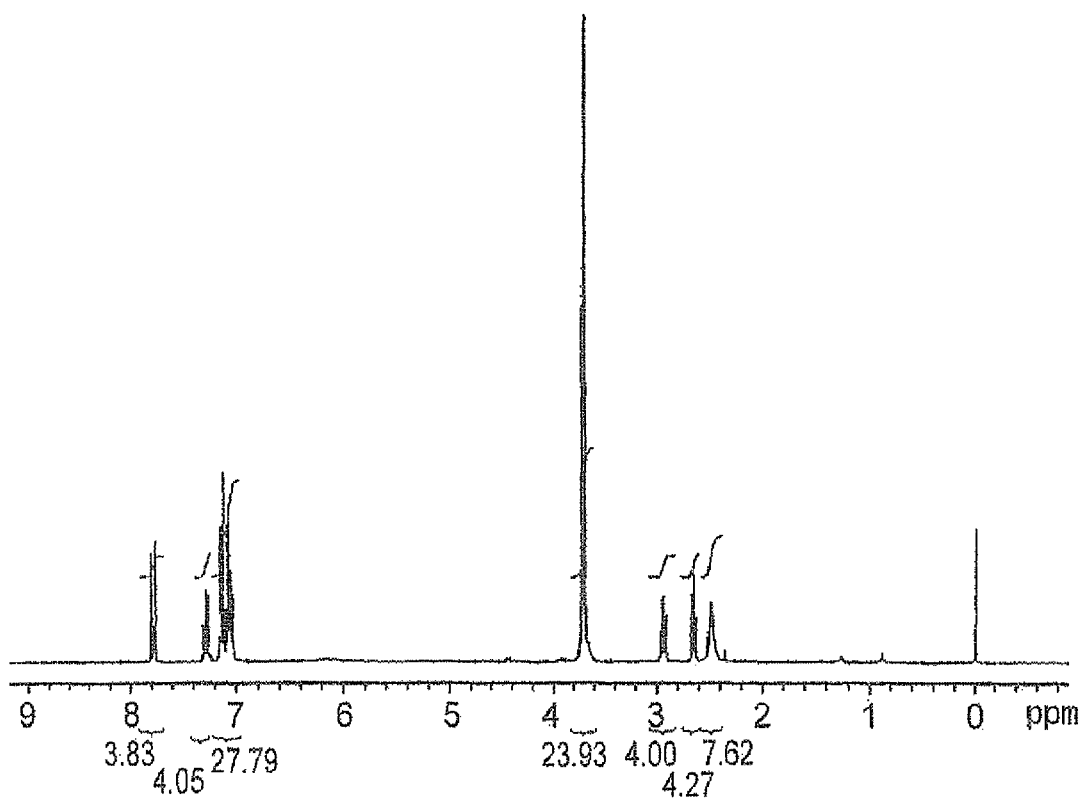
FIG. 6 is a $^1$H-NMR spectrum of the compound obtained in Example 3.

The infrared absorption spectrum of Exemplary compound 4 is shown in FIG. 5, and the $^1$H NMR spectrum thereof ($^1$H-NMR, solvent: CDCl$_3$, the same being applied correspondingly to any NMR spectrum in the following) is shown in FIG. 6.

The ionization potential of the compound of Exemplary compound 4 is 5.62 eV, the hole mobility thereof is $4.18 \times 10^{-6}$ cm$^2$/Vs, and the electron mobility thereof is $5.18 \times 10^{-6}$ cm$^2$/Vs.

Peaks in the IR spectrum obtained using ATR method reside at 695 cm$^{-1}$, 756 cm$^{-1}$, 835 cm$^{-1}$, 886 cm$^{-1}$, 1047 cm$^{-1}$, 1085 cm$^{-1}$, 1178 cm$^{-1}$, 1285 cm$^{-1}$, 1445 cm$^{-1}$, 1513 cm$^{-1}$, 1594 cm$^{-1}$, 1729 cm$^{-1}$, 2894 cm$^{-1}$, and 2947 cm$^{-1}$.

Peaks in the $^1$H-NMR spectrum using CDCl$_3$ solvent reside at 2.38-2.58, 2.62-2.71, 2.88-195, 3.65-3.85, 7.00-7.18, 7.22-7.38, and 7.74-7.82.

These results indicate that the Exemplary compounds obtained in the Examples are thiazolothiazole compounds having solubility and film forming property as well as both of hole transporting property and electron transporting property, and may be regarded as being useful in applications for various electric devices and the like. These results further indicate that the Exemplary compounds obtained in the Examples may be easily synthesized.

The foregoing description of the exemplary embodiments of the invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A thiazolothiazole compound represented by the following Formula (I):

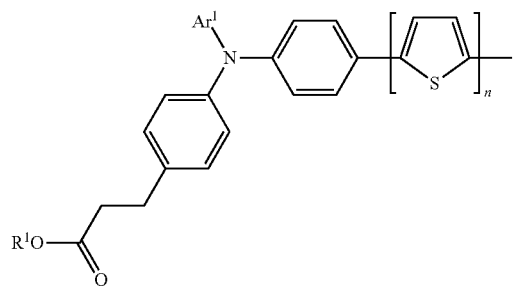

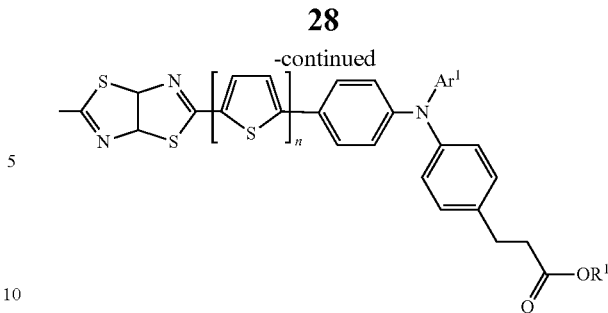

wherein each $Ar^1$ is the same and represents a substituted or unsubstituted aromatic group; each $R^1$ is the same and represents a hydrogen atom, an alkyl group, a substituted or unsubstituted aryl group, or a substituted or unsubstituted aralkyl group; and each n is the same and represents an integer of 0 or 1.

2. The thiazolothiazole compound of claim 1, wherein $Ar^1$ in Formula (I) represents one selected from the group consisting of: a substituted or unsubstituted phenyl group, a substituted or unsubstituted monovalent polynuclear aromatic hydrocarbon group having 2 to 20 aromatic rings, a substituted or unsubstituted monovalent condensed aromatic hydrocarbon group having 2 to 20 aromatic rings, a substituted or unsubstituted monovalent aromatic heterocyclic group, and a substituted or unsubstituted monovalent aromatic group having at least one aromatic heteroring.

3. The thiazolothiazole compound of claim 1, wherein $Ar^1$ in Formula (I) represents one selected from the group consisting of a substituted or unsubstituted phenyl group and a substituted or unsubstituted monovalent polynuclear aromatic hydrocarbon group.

4. The thiazolothiazole compound of claim 1, wherein $Ar^1$ in Formula (I) represents one selected from the group consisting of a substituted or unsubstituted phenyl group and a substituted or unsubstituted biphenylene group.

* * * * *